United States Patent
Schmidt et al.

(10) Patent No.: US 8,122,711 B2
(45) Date of Patent: Feb. 28, 2012

(54) PROCEDURE TO ACQUIRE A SOOTY PARTICLE CONCENTRATION IN THE EXHAUST GAS OF AN INTERNAL COMBUSTION ENGINE

(75) Inventors: Ralf Schmidt, Gerlingen (DE); Helmut Marx, Hochdorf (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 780 days.

(21) Appl. No.: 11/899,028

(22) Filed: Sep. 4, 2007

(65) Prior Publication Data

US 2008/0053067 A1 Mar. 6, 2008

(30) Foreign Application Priority Data

Sep. 5, 2006 (DE) .......................... 10 2006 041 478

(51) Int. Cl.
- *F01N 3/00* (2006.01)
- *G01N 21/00* (2006.01)
- *G01N 27/00* (2006.01)
- *G01N 31/00* (2006.01)
- *G01N 33/00* (2006.01)
- *G01N 35/00* (2006.01)
- *G01N 37/00* (2006.01)
- *G06F 19/00* (2011.01)
- *G06G 7/70* (2006.01)

(52) U.S. Cl. ............................. 60/297; 73/1.06; 701/114
(58) Field of Classification Search ................... 73/1.06; 701/114; 60/297

See application file for complete search history.

(56) References Cited

U.S. PATENT DOCUMENTS 7,334,401 B2 * 2/2008 Cheng .............................. 60/297

(Continued)

FOREIGN PATENT DOCUMENTS

DE 101 33 384 1/2003

(Continued)

*Primary Examiner* — Thomas Denion
*Assistant Examiner* — Michael Carton
(74) *Attorney, Agent, or Firm* — Merchant & Gould P.C

(57) ABSTRACT

The invention concerns a procedure to ascertain a concentration of sooty particles in an exhaust gas system of an internal combustion engine or a depletion of an emission control system of the internal combustion engine due to the loading of sooty particles, whereby the sooty particle concentration in the exhaust gas system is determined by means of a collecting particle sensor, which emits a sensor signal and whereby the depletion of the emission control system due to the loading of sooty particles is determined from the sooty particle concentration.

The task is thereby solved, in that the sensor signal is corrected by means of predetermined corrections with regard to a sensor temperature and/or an exhaust gas temperature and/or a flow velocity of the exhaust gas and/or a voltage applied at the particle sensor. Transverse sensibilities of the particle sensor can thereby be taken into account during the evaluation; and the determination of the accumulated loading of sooty particles and the determination of the sooty particle concentration in the exhaust gas system are improved. In the process, the sensor temperature enters into the correction to the extent that a temperature dependence of the electrical resistance of the loading of sooty particles is determined in a preparation phase and can be taken into account during the evaluation of the sensor signal.

8 Claims, 1 Drawing Sheet

U.S. PATENT DOCUMENTS

| | | | |
|---|---|---|---|
| 2004/0000139 A1* | 1/2004 | Kawashima et al. | 60/295 |
| 2004/0089544 A1* | 5/2004 | Kato et al. | 204/424 |
| 2007/0010932 A1* | 1/2007 | Gotoh et al. | 701/114 |
| 2007/0089478 A1* | 4/2007 | Wirth et al. | 73/1.06 |

FOREIGN PATENT DOCUMENTS

| | | |
|---|---|---|
| DE | 10 2005 034 247 | 1/2007 |
| DE | 10 2005 040 790 | 3/2007 |

* cited by examiner

PROCEDURE TO ACQUIRE A SOOTY PARTICLE CONCENTRATION IN THE EXHAUST GAS OF AN INTERNAL COMBUSTION ENGINE

BRIEF DESCRIPTION OF THE INVENTION

The invention concerns a procedure to acquire a sooty particle concentration in an exhaust gas system of an internal combustion engine or a loading of sooty particles in the emission control system of the internal combustion engine, whereby the sooty particle concentration in the exhaust gas system is determined by means of a collecting particle sensor, which emits a sensor signal, and whereby the loading of sooty particles in the emission control system is determined from the sooty particle concentration.

As a result of currently planned statutory regulations, the particle discharge of an internal combustion engine, especially of a diesel engine, must be monitored during a driving operation before and/or after a particle filter, as, for example, before and after a diesel particle filter. Moreover, a forecast concerning the degree of depletion of the diesel particle filter due to the loading of sooty particles is required for the regeneration check in order to be able to achieve a high degree of system security and to be able to deploy cost effective filter materials. Furthermore, provision can be made for a closed loop control of the combustion characteristics on the basis of information about the particle discharge. A resistive particle sensor is one possibility to measure the particle concentration in the exhaust gas. This particle sensor consists of finger-shaped, interlocking electrodes on a ceramic substrate. If sooty particles deposit on the electrode structure, the impedance of the mechanism changes. In the simplest case, the depletion due to the loading of sooty particles is evaluated using a measurement of resistance. To improve the likelihood of particles being deposited on the particle sensor, provision can be made for a trapping sheath in the area of the electrodes. According to the state of the art in one embodiment, a threshold is established for the resistance, respectively for a current flowing through the particle sensor at a known voltage; and the time is measured from the beginning of one measurement cycle with an unladen particle sensor up until this threshold value is achieved. After the threshold has been achieved, the particle sensor is heated up with the aid of an integrated heating element and is cleared of the accumulated sooty particles by oxidation, so that a new measurement cycle can be started. In another embodiment the resistance or current signal is determined in a variable or fixed grid of measurement periods and an increase of the resistance or current signal is determined.

Such a collecting, resistive particle sensor is described in the German patent DE 101 33 384 A1. The particle sensor is constructed from two interlocking, comb-shaped electrodes, which are at least partially covered by a trapping sheath. If particles from the exhaust gas of an internal combustion engine have accumulated on the particle sensor, this leads in turn to an assessable change of impedance of the particle sensor, from which a conclusion can be drawn about the amount of accumulated particles and consequently about the amount of particles carried in the exhaust gas.

Particle sensors have a large transverse sensitivity with regard to outside influencing variables, such as sensor temperature, exhaust gas temperature or even exhaust gas velocity. These variables thus influence the accumulation of the particles at the sensor as well as also the measured impedance of the sensor.

In application DE 10 2005 040 790.0, a procedure to operate a sensor for the acquisition of particles in an exhaust gas flow is described. In the application, at least one measurement for the exhaust gas flow at the particle sensor is ascertained; and in the evaluation of the particle sensor signal supplied by the particle sensor, the measurement for the exhaust gas flow is taken into account. Additional influencing variables on the transverse sensibilities of the sensors are not taken into account in the procedure described above.

In an additional application DE 10 2005 034 247.7, a procedure to monitor an exhaust gas threshold value of an internal combustion engine by means of an engine management system is described, whereby the engine management system has at least one exhaust gas sensor, and an error signal is emitted when the exhaust gas threshold value is exceeded. The emissions forecasted for the present operating state are thereby ascertained with the aid of an engine model and are compared with the signal of the exhaust gas sensor or with a comparative value for the emissions derived from it. The exhaust gas sensor can be a collecting particle sensor. The procedure allows for the monitoring of the exhaust gas with regard to driving cycles standardized with each other in order to establish the operating conditions of the internal combustion engine, which deviate from the threshold values.

It is the task of the invention to indicate a procedure to ascertain a particle concentration in the exhaust gas of an internal combustion engine, which allows for a more accurate determination of the depletion of an exhaust gas emission system resulting from the loading of sooty particles.

SUMMARY OF THE INVENTION

The task is thereby solved, in that the sensor signal is corrected by means of predetermined corrections with regard to a sensor temperature and/or an exhaust gas temperature and/or a flow velocity of the exhaust gas and/or a voltage applied at the particle sensor. In this way, transverse sensibilities of the particle sensor can be taken into account in the evaluation, and the determination of the accumulated loading of sooty particles and the concentration of sooty particles in the exhaust gas system are improved. In the process, the sensor temperature enters into the correction to the extent that a temperature dependency of the electrical resistance of the loading of sooty particles is determined in a preparation phase and can be taken into account during the evaluation of the sensor signal. Additionally the sensor temperature can be taken into account to the extent that an accumulation of particles on the particle sensor results as a function of the temperature difference between the exhaust gas and the sensor element. The exhaust gas temperature and the flow velocity of the exhaust gas at the site of the particle sensor likewise influence the probability of accumulation of particles at the particle sensor and can be taken into account. Furthermore, the exhaust gas temperature and the flow velocity of the exhaust gas influence the probability of accumulation in the emission control system, so that the forecast of the depletion of the emission control system due to the loading of sooty particles can be corrected with these variables. The voltage applied to the particle sensor influences the probability of accumulation and can for this reason be included in the correction. A correction due to the voltage applied at the particle sensor can be omitted if the voltage is kept constant.

If the voltage applied at the particle sensor is corrected with a drop in voltage at a dropping resistor used as a measuring resistor, the voltage present at the particle sensor and the current flowing through the particle sensor can be more accurately determined. Additionally, the influence of the voltage present at the particle sensor on the probability of accumulation can be taken into account.

If the sensor signal is corrected with a reduced probability of accumulation due to the voltage applied at the particle sensor, the determination of the particle concentrations in the exhaust gas system can be improved.

The influence of an accumulation of smut on the sensor signal can be corrected, in that the sensor signal is corrected with a predetermined maximum change per unit of time. Smut can lead to a precipitous change in the sensor signal, which can falsify the evaluation. This can be corrected by a limitation of the maximum allowed change per unit of time.

If the sensor signal is corrected using a temperature dependent conductivity of an accumulation of soot on the particle sensor, while taking into account the sensor temperature, the temperature dependence of the electrical resistance of the loading of sooty particles can be determined in a design phase and taken into account during the evaluation of the sensor signal.

Provision is made in an embodiment with a particularly reliable and robust determination of the particle concentration in the exhaust gas flow for the sensor signal to be accepted as an electrical current through the particle sensor. Provision is then also made for a current gradient to be established from the sensor signal by a signal smoothing and a formation of gradients.

Provision is made with an improvement of the accuracy of the determination of the particle concentrations in the exhaust gas for the sensor signal to be corrected with the flow velocity of the exhaust gas in the exhaust gas system and with an impact of a trapping sheath affixed in the area of a sensor face of the particle sensor.

If the sensor signal is corrected with the temperature difference between the exhaust gas temperature and the temperature of the particle sensor, the deposition velocity, which is dependent on the temperature difference, can be taken into account in the correction.

If the predicted depletion of the emission control system due to the loading of sooty particles is corrected with the exhaust gas temperature and/or the flow velocity of the exhaust gas in the exhaust gas system, the forecast can, thus, take into account these influences on the probability of accumulation and is thereby improved.

BRIEF DESCRIPTION OF THE DRAWINGS

The invention is described in detail below using one of the examples of embodiment depicted in the figures. The following are shown.

DETAILED DESCRIPTION OF THE DRAWINGS

Figure 1:
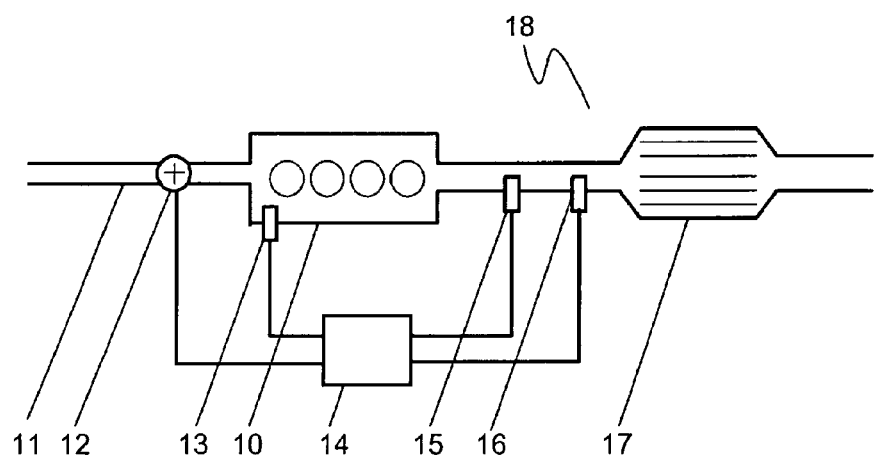
FIG. 1 an internal combustion engine with an emission control system.

FIG. 1 shows schematically the technical outer field, in which the procedure according to the invention can be applied. An internal combustion engine 10, which can be put into execution as a diesel motor, is delivered air for combustion by way of an air feed 11. In so doing, the amount of air for combustion can be determined by means of an air-flow meter 12 in the air feed 11. The amount of air can be used in a correction of a probability of accumulation of the particles present in the exhaust gas of the internal combustion engine 10. The exhaust gas of the internal combustion engine 10 is discharged via an exhaust gas system 18, in which an emission control system 17 is disposed. This emission control system 17 can be embodied as a diesel particle filter. Additionally a lambda probe 15 and a particle sensor 16, whose signals are supplied to an engine management system 14, are disposed in the exhaust gas system 18. The engine management system 14 is connected additionally to the air-flow meter 12 and determines on the basis of the data, which it is provided, a fuel amount, which can be delivered to the internal combustion engine 10 by way of a fuel metering 13. In one of the embodiments deviating from the one depicted in FIG. 1, the particle sensor 16 can also be disposed after the emission control system 17 in the direction of flow of the exhaust gas. With the devices depicted, a monitoring of the particle discharge of the internal combustion engine 10 (On Board Monitoring) and a forecast of the depletion of the emission control system 17 due to the loading of sooty particles are possible. The emission control system 17 is embodied in FIG. 1 as a diesel particle filter.

Figure 2:
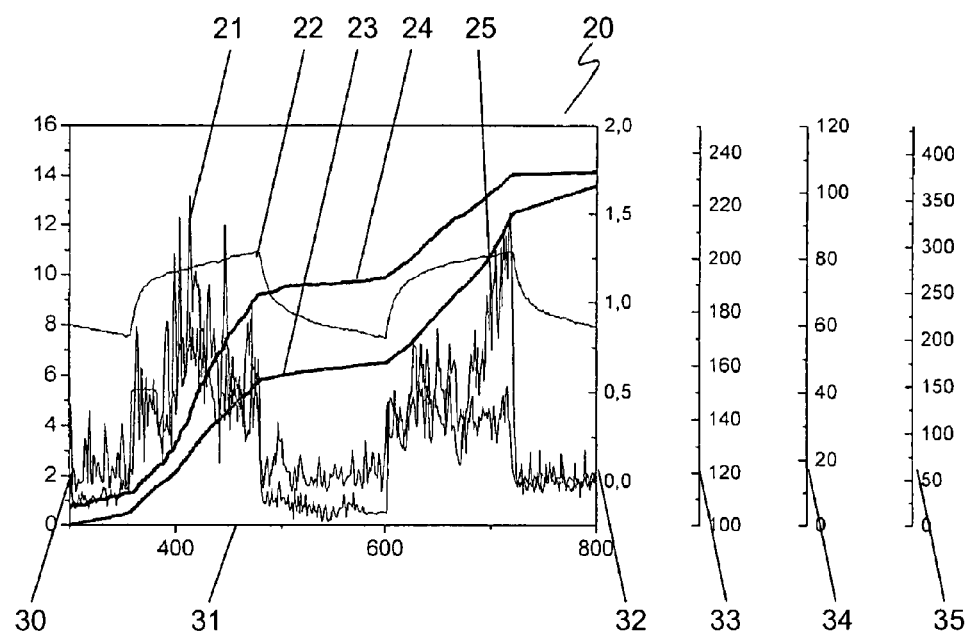
FIG. 2 a signal diagram for a particle sensor.

FIG. 2 shows a signal diagram 20 for the signals occurring at the particle sensor 16 and in its outer field as well as for the signals derived from these. The particle sensor 16 is designed as a collecting particle sensor 16 in the embodiment depicted. The particle sensor is stressed by the voltage across a dropping resistor used as a measuring resistor, so that a current arising by way of the electrically conductive loading of sooty particles can be used as an output signal.

The signals are marked off along a time axis 31. On a sensor signal axis 30, a sensor signal 24 is marked off in microamperes as electrical current through the particle sensor 16. A sensor signal slope 21 is determined from the sensor signal 24. This sensor signal slope 21 is marked off in random units along a sensor signal slope axis 32. A sooty particle concentration 25, which is plotted on a sooty particle concentration axis 34 in $mg/m^3$, is determined from the sensor signal 24 and the sensor signal slope 21. An exhaust gas temperature 22 is depicted along a temperature axis 33. A depletion of the emission control system 17 due to the loading of sooty particles 23, which is plotted in milligrams along a sooty particle loading axis 35, can be determined from the aforementioned variables and additional variables not depicted here. The depletion due to the loading of sooty particles 23 is an integral value, which would be deposited in a diesel particle filter. If the depletion due to the loading of sooty particles 23 reaches a predetermined threshold value, the emission control system 17 can be unloaded by way of an oxidation of the sooty particles. The signal for the concentration of sooty particles 25 allows for a monitoring of the operation of the internal combustion engine 10. It (the signal) can also be used for the On Board Diagnosis of the emission control system 17, which is embodied as a diesel particle filter, during the installation of the particle sensor 16 behind the emission control system 17.

The invention claimed is:

1. A method of ascertaining a sooty particle concentration with a collecting particle sensor in an exhaust gas system of an internal combustion engine and a depletion of an emission purification system of the internal combustion engine due to a loading of sooty particles, the method comprising:
   accepting a sensor signal as an electrical current through the collecting particle sensor and developing a current gradient from the sensor signal by a signal smoothing and a formation of gradients;
   determining the sooty particle concentration by a sensor signal emitted by the collecting particle sensor and the current gradient;
   determining the depletion of the emission purification system from the sooty particle concentration; and
   correcting the sensor signal through predetermined corrections of at least one of: a sensor temperature, an exhaust gas temperature, a flow velocity of the exhaust gas, and a voltage applied at the collecting particle sensor.

2. A method according to claim 1, further comprising correcting the voltage applied at the particle sensor with a voltage drop at a dropping resistor used as a measuring resistor.

3. A method according to claim 1, wherein correcting includes correcting the sensor signal with a reduced probability of concentration due to the voltage applied at the particle sensor.

4. A method according to claim 1, wherein correcting includes correcting the sensor signal with a predetermined maximum change per unit of time.

5. A method according to claim 1, wherein correcting includes correcting the sensor signal with a temperature dependent conductivity of an accumulation of sooty particles on the particle sensor while taking into account the sensor temperature.

6. A method according to claim 1, wherein correcting includes correcting the sensor signal with the flow velocity of the exhaust gas in the exhaust gas system and with an impact of a trapping sheath affixed in the area of a sensor face of the particle sensor.

7. A method according to claim 1, wherein correcting includes correcting the sensor signal with a temperature difference between the exhaust gas temperature and the temperature of the particle sensor.

8. A method according to claim 1, further comprising correcting a predicted depletion of the emission purification system due to the loading of sooty particles with the exhaust gas temperature, or the flow velocity of the exhaust gas in the exhaust gas system.

* * * * *